(12) United States Patent
Avila et al.

(10) Patent No.: US 6,649,815 B1
(45) Date of Patent: Nov. 18, 2003

(54) *LACTUCA SATIVA* CULTIVAR EXHIBITING RESISTANCE TO LETTUCE DROP (*SCLEROTINIA MINOR*) AND TIPBURN

(75) Inventors: Tony M. Avila, Salinas, CA (US); Adolfo S. Mederos, Salinas, CA (US)

(73) Assignee: Central Valley Seeds, Inc., Salinas, CA (US)

( * ) Notice: Subject to any disclaimer, the term of this patent is extended or adjusted under 35 U.S.C. 154(b) by 0 days.

(21) Appl. No.: 09/574,476

(22) Filed: May 19, 2000

(51) Int. Cl.[7] .............................. A01H 1/00; A01H 1/04; A01H 5/00; A01H 5/10
(52) U.S. Cl. ..................... 800/305; 800/260; 800/265
(58) Field of Search ................................ 800/305, 260, 800/265

(56) References Cited

U.S. PATENT DOCUMENTS

| | | | |
|---|---|---|---|
| 5,220,113 A | 6/1993 | Miltz | 800/200 |
| 5,684,226 A | 11/1997 | Sarreal | 800/200 |
| 5,973,232 A | 10/1999 | Waycott et al. | 800/305 |

*Primary Examiner*—David T. Fox
*Assistant Examiner*—Francis P. Moonan
(74) *Attorney, Agent, or Firm*—Jondle & Associates PC

(57) ABSTRACT

The present invention relates to a new Romaine (Cos) *Lactuca sativa* cultivar designated Green Forest, which exhibits resistance to lettuce drop and tipburn, a leaf color of Value 3 Chroma 4 Hue 7.5 GY according to the Munsel Color Chart for Plant Tissues and weighs about 4.7% more than the comparable varieties of Romaine Lettuce.

7 Claims, 1 Drawing Sheet

LACTUCA SATIVA CULTIVAR EXHIBITING RESISTANCE TO LETTUCE DROP (SCLEROTINIA MINOR) AND TIPBURN

BACKGROUND OF THE INVENTION

1. Field of the Invention

The present invention relates to a new *Lactuca sativa* romaine cultivar that exhibits resistance to lettuce drop (*Sclerotinia minor*) and tipburn.

2. Background of the Invention

Vegetables and especially lettuce have growing importance in the human diet. There are unique qualities to these foodstuffs that make them critically important to good health and longevity of life. Such vegetables are nearly exclusive eaten in their natural state as a fresh, raw product. As such the appearance of such vegetables is critical to their sale. Americans especially demand a perfect or near perfect appearance of their raw products. Whereas, in some countries, foodstuffs can have blemishes and imperfections and be fit for the market, the US consumer demands a perfect near unblemished product.

Additionally, Americans are very demanding of the color of their food. Various shades of color can determine whether a food product is successful at market. A deeper shade of green looks more appetizing than a pale shade of green or a green with a yellowish tint. A deep green in a ripe, healthy head of lettuce is especially desirable in a Romaine lettuce and its varieties and has been found to be especially strong commercially.

It will be appreciated that all growers are faced with a limited amount of space in which to grow their vegetables and food products. It is more than desirable to maximize the yield of a particular parcel and especially so for the small to moderate sized grower. For example, if a grower can break even by selling about 500 cartons of lettuce per acre and he can switch to a different variety of the same lettuce and grow about 900 cartons of lettuce per acre, the product of the different variety would be much more valuable. This very well could be the difference between a grower able to survive bad economic conditions one year and continue his operation or going under and being forced to sell out or turn his land into residential property.

The export of vegetables across the international and state lines is vital to the grower and shippers of fresh produce. In fact, California and Arizona grow about 90% of the total United States lettuce production and It is estimated that about 75% or more of all lettuce grown in California is so exported (Subbaroa 1998) for sale in states such as New York, Pennsylvania, Massachusetts and the like.

It is also traditional to export lettuce. Originally, lettuce was trucked from one location to another using ice to keep the lettuce fresh. This is how the name "iceberg" lettuce came into being. Thus, not only is lettuce exported from the growing regions, but it has been so in the past and is likely to being for many future years as well.

For a further understanding of lettuce, its uses and history Waycott et al, U.S. Pat. No. 5,973,232 and Subbaroa 1998 is incorporated herein by references.

There are six morphological types of lettuce: crisphead (iceberg), butterhead, Cos (Romaine), leaf, stem and Latin. The crisphead is the most common in the United States, while butterhead and Romaine types are popular in northern and southern Europe. Id Lettuce originated from the ancestral wild species *L. sativa*. Today there are over one hundred cultivars, which are divided in commerce into four large groups based on gross morphological characteristics of the gross leaf morphology and leaf arrangement (Subbaroa 1998). These basic lettuce types frequently form the basis for grouping lettuces as is commonly seen in supermarkets, grocery and produce stores. Each of these basic groups is comprised of numerous cultivars; each characterized by its own particular morphology, disease resistance, and cultural adaptations.

Lettuce cultivars are susceptible to a number of diseases such as downy mildew (*Bremia lactucae*), lettuce drop (*Sclerotinia minor* and *S. sclerotiorum*), corky root (*Rhizomonas suberifaciens*), lettuce mosaic virus, big vein, and aster yellows, just to list a few. These diseases result in millions of dollars of lost lettuce crop through the world every year. In California alone, the average seasonal losses by lettuce drop, caused by *Sclerotinia minor* or *Sclerotinia sclerotiorum*, is about 15% and may reach to about 60% or higher with heavy economic losses at higher lettuce prices. Lettuce drop effects all types of lettuce. There is no effective means of controlling lettuce drop and breeding host resistance cultivars remains the only logical option to manage the epidemiology of the disease.

The market quality of lettuce may also be influenced by abiotic factors. Tipburn disorder is one example. Tipburn incidence in lettuce is characterized by the presence of necrotic lesions at or near the margins of rapidly expanding inner enclosing mature leaves (Ryder 1998). Tipburn reaction is possibly related to a deficiency in plant calcium transport system along with reduced transpiration due to inner leaf enclosure. Inefficient concentration of calcium in the margins of rapidly expanding leaves may lead to cell wall breakdown and the occurrence of large to small lesion formation (Collier and Tibbitts 1982, Barta & Tibbitts 2000). Depending on the severity of tipburn at harvest time, the grower may be entitled to lower market price or loss of the entire crop. Development of tipburn injury symptoms may occur when the daytime temperature ranges from 32 to 40° C. (Ryder 1998). Plants may exhibit considerable tipburn injury at or near the market stage especially when the inner mature leaves have completely enclosed or cupped in. Lettuce cultivars with resistance to tipburn are highly desired by the growers.

In order for lettuce to be fit to travel to other states it must pass a vigorous inspection. A part of the inspection calls for the lettuce plants to be free of rot, decay or tipburn. Even a small amount of rot or tipburn can open the door to an infection for the entire shipment. Thus, not just the infected plant or plant(s) are banned from travel across state lines, but the entire lot of lettuce will be prohibited should evidence of such lettuce drop or tipburn be found.

In order to be commercially viable, a grower must then be able to produce a sufficient quantity of plants that are healthy and fit for travel. The yield of the grower's acreage will determine the grower's financial success and whether he can continue his operation in the face of rising competition and market driven demands.

What is therefore needed is a lettuce plant variety that allows the grower to maximize his yield and provide plants that are desirable to the consuming public. It is also desirable to provide the lettuce grower with a lettuce plant that not only maximizes his yield, but also yields a plant, which is fit for travel across interstate lines. And, it is desirable to provide the lettuce grower with a lettuce plant which generates strong consumer sales by having the sought after color and appearance.

SUMMARY OF THE INVENTION

It is a general object of this invention to provide a new Romaine *Lactuca sativa* cultivar, which increases yield to growers.

It is another object of this invention to provide a new Romaine *Lactuca sativa* cultivar, which not only increases yield but also provides a pleasing and commercially desirable dark green color.

The present invention comprises a new Romaine *Lactuca sativa* cultivar referred to as Green Forest. Green Forest exhibits increased resistance to lettuce drop and tipburn. In addition, Green Forest has a leaf color of Value 3 Chroma 4 Hue 7.5 GY according to the Munsel Color Chart for Plant Tissues. Furthermore, Green Forest weighs about 4.7% more than the comparable varieties of Romaine Lettuce. Specifically, in average mature heads of Green Forest weigh about 781 grams compared to 744 grams for the closest comparable variety, Darkland Cos (Plant Variety Protection Certificate No. 9000137), which is commercially available from Central Valley Seeds, Incorporated. Seeds of Green Forest has been deposited with a public depository agency the American Type Culture Collection (ATCC), 10801 University Boulevard, Manassas, Va. 20110-2209 under the Budapest treaty on May 3, 2000 and has assigned Accession number PTA-1805. In addition, a Plant Variety Protection Certificate has been applied with the United States Department of Agriculture and has received the application No. 200000013.

The present invention relates to a *Lactuca sativa* plant produced by growing the seed of Green Forest that has ATCC Accession No. PTA-1805 The present invention also relates to a *Lactuca sativa* plant that has all the physiological and morphological characteristics of a *Lactuca sativa* plant grown from seed on ATCC PTA-1805.

Finally, the present invention relates to a hybrid *Lactuca sativa* plant having Green Forest as a parent.

DETAILED DESCRIPTION OF THE INVENTION

Definitions

Figure 1:
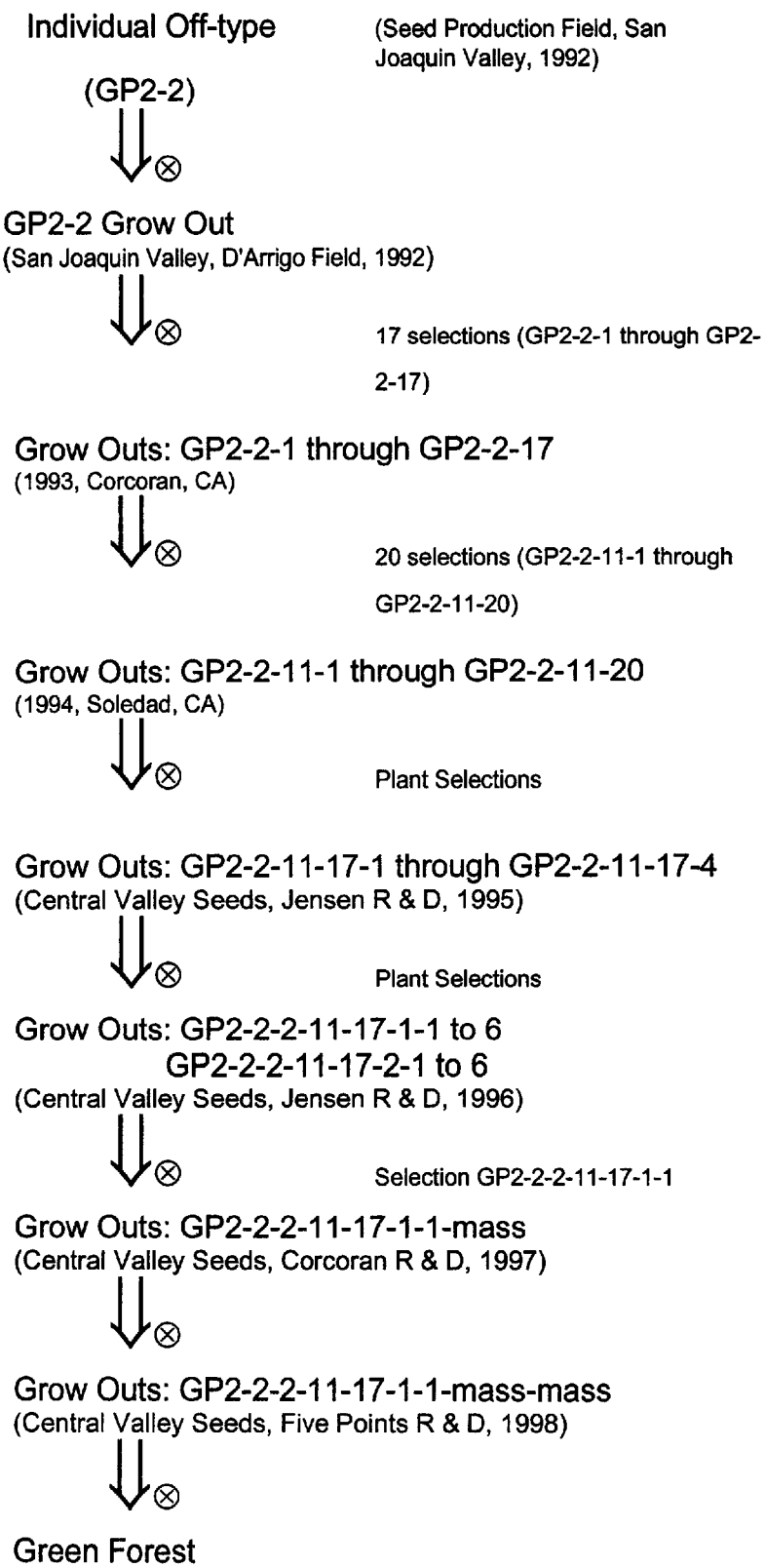
FIG. 1 illustrates the origin and breeding history of green forest.

The following definitions will be helpful in the discussion of Green Forest cultivar that follows.

Cotyledon. In the case of lettuce, one of a pair of leaves formed on an embryo within a seed, which upon germination are the first leaves to emerge.

Fourth Leaf. The fourth leaf formed on the lettuce plantlet subsequent to the emergence of the cotyledons.

Frame Leaf. The first set of freely recurring leaves which are external to the head.

Market Stage. The developmental stage reached by a crop plant at which time the plant is ready for harvest. In Iceberg Group cultivars of lettuce, it is that stage at which the head has reached a maximum size before bolting but in which most of the head leaves are still tightly clasping.

Butt. The bottom portion of the lettuce which includes the stem and adjacent leaf bases of the outermost head leaves.

Core. The stem of the lettuce head on which the leaves are borne.

Bolt. The process during which the stem within the lettuce head greatly elongates, causing the head to lose its shape and resulting ultimately in the producing of a flowering stalk.

Origin and Parentage of Green Forest

Referring now to FIG. 1, the genealogy of lettuce cultivar of the present invention, herein designated, as Green Forest will now be described. Green Forest is a Cos or Romaine lettuce variety. Green Forest was brought into existence from a single black-seeded plant growing amongst the white-seeded Oasis crisphead seed production field of Central Valley Seeds, Inc. in San Joaquin Valley, Calif. The original plant selection was solely based on the presence of a black-seeded lettuce off-type with semi-Romaine leaf structures growing in the midst of white seeded crisphead seed production field. The selected plant was labeled as GP2-2 and was allowed to self pollinate and the resulting seeds were collected.

In the fall of 1992, about 60 plants of GP2-2 were grown in San Joaquin Valley. A few crisphead type (numbers not available) was observed in this grow out. Seventeen Romaine plants were selected for having dark green leaf color extended plant height, thick and savoyed leaf texture with smooth leaf undulation and resistance to tipburn. The selected plants were labeled as GP2-2-1 through GP2-2-17 and were allowed to self pollinate and the resulting seeds were collected.

In 1993, seeds of the above 17 selections were planted in a field trial for further evaluation. Phenotypic segregation for leaf type and color was prevalent amongst the breeding lines. Total of 20 plants, labeled as GP2-2-11-1 through GP2-2-11-20, were tagged and selected from line GP2-2-11 for having extremely dark green leaf color, thick leaf texture, savoyed with smooth leaf undulation, extended plant height, resistance to tipburn, and absence of suckering and leaf cupping. These plants were allowed to self pollinate. The resulting seeds were collected.

In March of 1994, the seeds of the 20 breeding lines were planted in the Central Valley Seeds' Soledad, Calif. R & D field. A fair degree of differences for leaf color, leaf texture and plant height appeared among the lines. Plant selection was limited to a few outstanding lines that were judged to be phenotvpically more uniform. The selections were as follows:

| Breeding Line | No. of Selections |
| --- | --- |
| GP2-2-11-7 | 4 |
| GP2-2-11-8 | 4 |
| GP2-2-11-16 | 4 |
| GP2-2-11-17 | 4 |
| GP2-2-11-19 | 3 |
| GP2-2-11-20 | 4 |

Selection criteria from each breeding lines was primarily based on plants having extremely dark green leaf color, thick leaf texture, savoyed with smooth leaf undulation, extended plant height, resistance to tipburn, short to medium core length and absence of suckering and leaf cupping. Plants from each selection were tagged accordingly and were allowed to self pollinate and the resulting seeds were collected.

In 1995, seeds of the selfed plants labeled as GP2-2-11-17-1 through GP2-2-11-17-4, were planted in Central Valley Seeds' Jensen R & D field trial. Plants from each line were appeared to be uniform in height and genetically invariable for color and core length. Additional selections were made from the following lines:

| Breeding Line | No. of Selections |
| --- | --- |
| GP2-2-11-1 7-1 | 6 |
| GP2-2-11-17-2 | 6 |

| Breeding Line | No. of Selections |
|---|---|
| GP2-2-11-17-3 | 6 |
| GP2-2-11-17-4 | 6 |

Each selection was tagged accordingly and was allowed to self again.

In 1996, seeds of lines GP2-2-11-17-1 and GP2-2-11-17-2 breeding lines were planted in a field trial. Plants of each line were extremely uniform for our selection criteria without the presence of any segregants, off types or variants. Plants of line GP2-2-11-17-1-1 were massed due to their favorable phenotypic and field appearances. Altogether, plants of GP2-2-11-17-1-1 breeding line appeared to express very dark green leaf color, thick leaf texture, savoyed with smooth leaf undulation, extended height, resistance to tipburn, short to medium core length and absence of suckering and leaf cupping. Plants of the selected breeding line were labeled as GP2-2-11-17-1-1-mass and allowed to self pollinate and the resulting seeds were collected.

In 1997, seeds of GP2-2-11-17-1-1-mass were planted in Central Valley Seeds' Corcoran, California field/production trial for further evaluation. Plants were extremely uniform for having very dark green leaf color, thick leaf texture, savoyed with smooth leaf undulation, extended height, resistance to tipburn, short to medium core length and absence of suckering and leaf cupping. No segregants, off types or variants were observed among the examined breeding line. No single plant selection was made. The entire line was labeled as GP2-2-11-17-1-1-mass-mass and the plants were allowed to self pollinate. The resulting seeds were collected.

In 1998, seeds of the GP2-2-11-17-1-1-mass-mass were planted in Central Valley Seeds' Five Points, Calif. field/production trial. Plants were exceptionally uniform for very dark green leaf color, thick leaf texture, savoyed with smooth leaf undulation, extended height, resistance to tipburn, short to medium core length and absence of suckering and leaf cupping. No segregants, off types or variants were observed among the examined breeding line.

Based on the field data and observations the inventors believe that Green Forest is able to endure higher than normal temperatures to produce a crop without or the least amount of tipburn five to seven days after internal cupping and post market stage. Under higher than normal heat midribs and leaves of most of the commercial Romaine varieties may become spiral, twisted or pale in color. No such adverse effect has been observed in field trials of Green Forest.

Additionally, the inventors of the present invention believe that Green Forest is significantly less vulnerable to lettuce drop caused by the *Sclerotinia minor* fungus. The lettuce drop fungus is widely distributed wherever lettuce is grown and the degree of infection rate and crop losses is highly associated with soil type and elevated moisture content especially along the coastal lettuce producing regions of California. Under such high moisture conditions, one may find the *S. minor* fungus on the lower surface of the infected plant leaves lying flat on the soil surface and attacking the crown of the plant. Therefore, lettuce plants having leaves with minimal soil contact may exhibit very low lettuce drop symptoms. The inventors of the present invention believe that frame leaves, the first set of freely recurring leaves that are external to the plant, of Green Forest grow in an upright position having very minimal soil contact, minimizing the ideal environment for the lettuce drop fungus to develop.

Additionally, in our judgment, Green Forest appears to be sweeter in taste and flavor compared to the available commercial varieties.

The experimental designated breeding line GP2-2-11-17-1-1-mass-mass was given the name Green Forest and has been suggested for commercial planting as a Cos or Romaine cultivar in California and Arizona. Green Forest lettuce variety is distinct, genetically stable and uniform. After eight generations no variants or off types have been observed in commercial fields and seed production trials.

Screening for Resistance to Lettuce Drop (*S. minor*)

Varieties were evaluated for resistance to lettuce drop caused by *S. minor* in the commercial fields. Infection of lettuce by *S. minor* may occur at any plant growth stage. To define resistance, evaluation of the test plots was carried out at the harvest or the market stage, which is considered to be the economically significant phase of the infection (Subbarao 1998). Plants were evaluated based on visible Lettuce drop symptoms. Symptoms may include rapid plant wilt, decay, and dying or complete death of the plant. Plants were considered dead when the entire plant has collapsed or dying when the outermost leaves appeared yellow in color and in the process of wilting. The presence of watery fungal decay at the crown or basal portion of the plant confirmed the presence of *S. minor* as the causal agent of lettuce drop in each test plot evaluation. Rating for resistance or susceptibility was based on the percentage of survived and harvestable disease-free plants. In all test plots, the Green Forest was grown side by side of the commercially planted variety(s), which was used as a control.

TABLE 1

Evaluation of Green Forest with similar varieties for Lettuce Drop disease resistance.

| Variety | Source | Percent dying |
|---|---|---|
| Darkland Cos | Central Valley Seeds, Inc. | 18.8 |
| Green Forest | Central Valley Seeds, Inc. | 7.4 |
| Green Towers | Harris Moran Seed Company | 16.6 |
| Hearts Delight | Coastal Seed Company | 39.1 |
| Big Heart | Progeny Seed Company | 11.3 |

Total of 10 different field locations. Survey of over 100 plants per trial per location with at least two replications. Not all locations had the same varieties but Green Forest was present in all field trials.

TABLE 2

Significant Differences:
ANOVA*:
Darkland Cos vs. Green Forest

|  | SS | df | MS | p[F] |
|---|---|---|---|---|
| Total | 2139.74 | 35 |  |  |
| Line | 1337.94 | 1 | 1337.94 | 0.000 |
| Location | 527.66 | 5 | 105.532 | 0.000 |
| Error | 274.14 | 29 | 9.45297 |  |

*The analyses were done using percent dying in an AnOVa, each AnOVa between two lines only (no locations had all varieties).
Green Forest was significantly different from all others.
There was no significant difference between Darkland Cos and Green Towers.
There was no significant difference between Green Towers and Hearts Delight.

Data Comparison

Big Heart was compared to Darkland Cos, Green Towers and Hearts Delight. Hearts Delight was compared to Darkland Cos and Big Heart. There was at least one significant difference between locations, the location effects removed.

Screening for Resistance to Tipburn

Selection for resistance to tipburn was made after internal cupping of the inner leaves. Crop evaluation was performed generally five to seven days post harvest or at market stage when the selection for tipburn resistance can be highly effected. In each test plot, approximately 10 plants per entry per trail were cut open and the margins of internal leaves were carefully examined for tipburn lesions, which usually ranged from large severe lesions to minimal or no lesion formation. Each plant was carefully evaluated and was rated for tipburn as follows: 0=no visible signs of tipburn, 1=little lesions (slight/beginning of tipburn at the leaf margins), 2=large severe lesions (tipburn at the leaf margin about 5 cm deep & 2–3 cm in length).

TABLE 3

Analysis of Resistance to Tip burn
Method 1. Pairwise t tests among common areas:

|  | Clemente | Darkland Cos | Green Forest | Green Towers | King Henry | Medallion | Prara Cos |
| --- | --- | --- | --- | --- | --- | --- | --- |
| Clemente |  | 0.353 | 0.011 | x | x | 0.742 | 0.038 |
| Darkland Cos |  |  | 0.001 | 0.742 | x | 0.742 | 0.019 |
| Green Forest |  |  |  | 0.057 | x | 0.020 | 0.006 |
| Green Towers |  |  |  |  | x | x | x |
| King Henry |  | pairwise t |  |  |  | x | x |
| Medallion |  |  |  |  |  |  | 0.170 |
| Prara Cos |  |  |  |  |  |  |  |

Total of 12 different field locations. Survey of 10 plants per trial per location. Green Forest is significantly different from Clemente, Darkland Cos, Medallion, and Prara Cos.

TABLE 4

Analysis of Resistance to Tip burn
Method 2. Chi-square tests

| Green Forest Green Towers | ρ = 0.005 |
| --- | --- |
| Green Forest King Henry | ρ = 0.005 |

Green Forest is significantly different from all of the six other lines.

Morphological Description of Green Forest

The lettuce cultivar Green Forest will now be described. The terminology used herein to describe Green Forest are those used by the United States Department of Agriculture, unless otherwise noted, in USDA Form LS-470-1, "Objective Description of Variety Lettuce *Lactuca sativa*."

1. PLANT TYPE. Green Forest is a Cos or Romaine type cultivar
2. SEED. Seed is black (Gray Brown).
3. COTYLEDON TO FOURTH LEAF STAGE. Cotyledons upon emergence are broad. The fourth leaf is ovate with a length/width index (L/WX10) of 11, without dentate apical margin. The fourth leaf is further characterized by being flat, without rolling, cupping, reflexing, yellow green color without anthocyanic expression.
4. MATURE LEAVES. Incision depth is absent as in the cultivar Dark Green Boston without undulation of the apical margin, dark green in color Value 3 Chroma 4 Hue 7.5 GY according to the Munsel Color Chart for Plant Tissues without anthocyanic expression. The leaves were large, glossy and thick without blistering; leaf trichomes were absent.
5. PLANT AT MARKET STAGE. Frame leaves have a spread of 28 cm. The heads are loose, large, weighing 838 grams with a standard deviation of 94 grams and a 24-head count per carton.
6. BUTT (BOTTOM OF MARKET-TRIMMED HEAD). The butt is tapered and flattened.
7. CORE (STEM OF MARKET TRIMMED HEAD). The core has a diameter at the base of the head of 45 mm and height (measured from the base to the head) of 65 mm.
8. BOLTING. Green Forest is a medium bolter compared to Darkland Cos taking approximately 68 days to bolt as measured from the time the seed first receives water sufficient for germination. The mature seed stalk reaches 112 cm in length, with a total spread of the bolted plant reaching 32 cm. The bolter leaves are dark green, straight and without dentate margins. Terminal inflorescence is absent with later and basal shoots.
9. MATURITY. Green Forest was Spring planted in Salinas, Calif. from 2–5 through 5–16; Summer planted in Salinas, Calif. from 5–13 through 7–6; Fall planted in Yuma, Ariz. from 9–26 through 10–15; Winter planted in San Joaquin Valley, Calif. from 11–15 through 12–25 and Yuma, Ariz. from 11–10 through 12–10. Spring plantings were matured to market-ready stage in about 91 days as compared to 95 days for Darkland Cos; Summer plantings were matured to market-ready stage in 53 days as compared to 57 days for Darkland Cos.
10. ADAPTION. Green Forest is adapted for planting in the Southwest (Calf. Ariz. Desert), West Coast, North-central and Northeast areas of the United States in mineral an organic soils.
11. DISEASE AND STRESS REACTIONS. Green Forest is highly resistant to *Sclerotinia minor* and tipburn.

Propagation of Green Forest

Green Forest may be propagated from seed or by tissue culture techniques.

Seed production is achieved by sowing existing seed in flats at 68°–70° F. Seedlings or young plantlets are then transferred to containers or beds and are grown at 85°–95° F. to induce bolting. Plants are allowed to self and the resulting seed are then collected.

Propagation may be had using explant material to produce leaf callus which is subsequently induced to from plantlets according to the methods described in Alconero, R. Hortscience 18:305–307 (1983), the contents of which are expressly incorporated herein.

Axial buds can be excised from existing plants and then can be induced to form rooted plants using in vitro culture techniques.

Production Methods of Green Forest

Production of market ready lettuce from Green Forest proceeds as follows. Seed is directly sown on double row beds of 40-inch centers. Rows on a bed are about 12 in. apart with seed deposited at intervals of 2 to 3 in. along the row.

Each seed is usually encapsulated in, or "pelleted," with inert clays to form a large and uniform pill. Encapsulation in this way facilitates positioning and planting of the seed which is small.

In California, the plants are watered during the germination phase using sprinkler systems. As the plants mature, watering is accomplished by irrigating the furrows between the rows.

Four to six weeks after germination, lettuce is thinned to produce a final stand in which plantlets are spaced apart in the row at distances of about 10 in.

In mineral soils common in the west, fertilization with nitrogen, phosphorus and, less frequently, potassium is required.

Harvest time varies according to the local climatic conditions. Green Forest takes approximately 53 days from planting to harvest in the coastal valleys of California in summertime.

Deposit of Green Forest

Seeds of Green Forest have been deposited with the ATCC. The deposit was made on May 3, 2000 and received accession number ATCC PTA-1805.

Although the cultivar of the forgoing invention has been described and illustrated, it should be understood that certain changes and modifications may be practiced within the scope of this invention without departing from the scope of the invention as set forth in the accompanying claims. All restrictions upon availability to the public of the deposit made to ATCC of the above identified plant will be irrevocably removed upon the granting of the patent.

While the foregoing detailed description has described several embodiments of the plant variety in accordance with this invention, it is to be understood that the above description is illustrative only and not limiting of the disclosed invention. Particularly, a range of dark green color is considered within the spirit and scope of the invention. Additionally, a range of resistance to both lettuce drop (*Sclerotinia minor*) and tipburn is also considered within the range of patentable subject matter that is also considered to within the spirit and scope of this invention. It will be appreciated that the embodiments discussed above and the virtually infinite embodiments that are not mentioned could easily be within the scope and spirit of this invention. Thus, the invention is to be limited only by the claims as set forth below.

References

Barta, D. J. and T. Tibbitts (2000). Calcium Localization and Tipburn Development In Lettuce Leaves During Early Enlargement. J. Amer. Hort. Sci. 125(3):294–298.

Collier, G. F. and T. Tibbitts (1982). Tipburn of Lettuce. Hort. Rev. 4:49–65.

Munsel Color Chart for Plant Tissues (1968). $2^{nd}$ Edition. Munsel Color Company, Inc. Baltimore, Md., USA.

Ryder, E. J. and W. Waycot (1988). Crisphead Lettuce Resistant to Tiburn: Cultivar Tiber And Eight Breeding Lines. Hortscience 33(5): 903–904.

Subbarao, K. V. (1988) Progress Toward Integrated Management of Lettuce Drop. Plant Disease 82(10) 1068–1078.

What is claimed is:

1. *Lactuca sativa* seed designated as Green Forest having ATCC Accession No. PTA-1805.

2. A *Lactuca sativa* plant produced by growing the seed of claim 1.

3. A *Lactuca sativa* plant having all the physiological and morphological characteristics of the *Lactuca sativa* plant of claim 2.

4. Propagation material of the plant of claim 1.

5. Pollen of the plant of claim 1.

6. Seeds of the plant of claim 1.

7. A hybrid *Lactuca sativa* plant having Green Forest as a parent, wherein Green Forest is grown from seed having ATCC Accession No. PTA-1805.

* * * * *